United States Patent [19]

Oishi et al.

[11] Patent Number: 5,039,524
[45] Date of Patent: Aug. 13, 1991

[54] VERMIN-REPELLENT MICROCAPSULES WITH SLOW-RELEASE POTENTIALITY

[75] Inventors: Ryuichi Oishi, Tokyo; Keiichi Utaka, Kodaira; Kumiko Ono, Fuchu; Michihiro Ohki; Toshirou Yasue, both of Tokyo, all of Japan

[73] Assignees: Toppan Moore Company, Ltd.; Showa Denko Kabushiki Kaisha, both of Tokyo, Japan

[21] Appl. No.: 227,506

[22] Filed: Aug. 2, 1988

[30] Foreign Application Priority Data

Jul. 1, 1988 [JP] Japan .................. 63-164380

[51] Int. Cl.$^5$ .................. A01N 25/28; B01J 13/18
[52] U.S. Cl. .................. 424/408; 424/457; 424/501; 424/DIG. 10; 428/402.21; 514/963
[58] Field of Search .................. 428/402.21; 424/408, 424/457, 501, DIG. 10; 514/963

[56] References Cited

U.S. PATENT DOCUMENTS

| | | | |
|---|---|---|---|
| 3,516,941 | 6/1970 | Matson | 428/402.21 |
| 4,353,962 | 10/1982 | Himel et al. | 428/407 |
| 4,456,569 | 6/1984 | Rodson et al. | 525/58 X |
| 4,557,755 | 12/1985 | Takahashi et al. | 428/402.21 X |
| 4,808,408 | 2/1989 | Baker et al. | 428/418 X |

Primary Examiner—Richard D. Lovering
Attorney, Agent, or Firm—Weingarten, Schurgin, Gagnebin & Hayes

[57] ABSTRACT

Disclosed are slow-release vermin-repellent microcapsules composed of a core substance and a wall film formed around the said core substance to encapsulate the same, in which the core substance is diethyltoluamide of a formula:

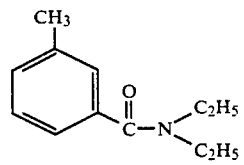

and the wall film has a function of slow-releasability.

3 Claims, No Drawings

VERMIN-REPELLENT MICROCAPSULES WITH SLOW-RELEASE POTENTIALITY

BACKGROUND OF THE INVENTION (1) Field of the Invention

The present invention relates to microcapsules filled with N,N-diethyl m-toluamide (hereinafter referred to as "diethyltoluamide") of a formula:

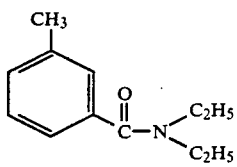

More precisely, it relates to microcapsules filled with diethyltoluamide which is effective as a repellent to insanitary vermine of a broad range, such as mosquitos, gnats, lies, horseflies, cockroaches, fleas, tsutsugamushi mites and acarids, and the microcapsules are improved to be free from the defect in use of the original diethyltoluamide.

(2) Description of the Prior Art

Insects of 1,800,000 kinds or more are known, and these include a group or so-called insanitary insects (vermin) which have directly or indirectly some bad influences on a human life.

Insanitary vermin typically include the following kinds:

Mosquitos which bite human and animal bodies to cause extreme itch, erubescence and swelling on the bitten skins and which carry various infectious diseases of Japanese B encephalitis, dengue, yellow fever, malaria, filariasis or the like; gnats, horseflies and rice-bran mosquitos whose female imagoes extremely bite human and animal bodies to often carry infectious diseases; cockroaches which carry infectious disease bacteria such as cholera bacillus, typhoid bacillus or dysentery bacillus as well as other pathogenic bacteria such as tubercle bacillus; tsutsugamushi mites to cause tsutsugamushi disease; and acarids which extremely bite human and animal bodies to such blood therefrom and which cause allergy disease. In addition, insanitary vermin further include clothes vermin such as clothes moths or webbing clothes moths, as well as fleas, flies and ants.

It is well known that diethyltoluamide is effective as a chemical agent for repelling the said insanitary vermin, but unfortunately, diethyltoluamide is defective in that this is poor in a long-time durability. Under the present situation, therefore, it is earnesly desired to overcome the said defect and to prolong the durability of the pharmaceutical potency of diethyltoluamide as long as possible. For the purpose, some means have heretofore been investigated, all of which, however, were insufficient.

As a method of killing insanitary vermin, spraying of an insecticide as well as use of an aerosol or fumigant containing an insecticide as an active ingredient is generally carried out. However, use of an insecticide of a high concentration is presumed to have some bad influence on human bodies, and in addition, it has various problems that vermin would again come to the treated region when the effective potency of the insecticide has vanished with the lapse of a certain period of time after the insecticide was applied to the region, vermin would have a chemical resistance to the insecticide after repeated and continuous application of the same insecticide to the same place so that the insecticide becomes ineffective to the resulting chemical-resistant vermin, and the died vermin are required to be taken away.

As one method for evading the said problems, an insanitary vermin repellent has heretofore been studied, and a lot of substances effective as a vermin-repellent have been found which include, for example, diethyltoluamide, N-butylacetanilide, 2-ethyl-1,3-hexanediol, 2-butyl-2-ethyl-1,3-propanediol and propyl mandelate. Among these repllents, diethyltoluamide is considered to be the most ideal repellent at the present time because of the reasons that the scope of the objects to be repelled thereby is broad, the safety is high, this hardly drops from clothes after applied thereto, this is excellent in the proofness to sweat and water and this has no odor offensive to human.

As means of using diethyltoluamide, there are known the following ways: Briefly, this is used in the form of a preparation of an aerosol, cream or lotion as a vermin-repellent for application to human bodies; diethyltoluamide of its original form is dissolved in a pertinent solvent or latex and coated, penetrated or incorporated into pile yarns, base clothes or packing materials of carpets so as to repell acarids or other vermin therefrom; or diethyltoluamide is penetrated into parts of the ceiling, side walls and drawers of clothes cabinets or parts of plate-racks to obtain vermin-repellent furnitures and plate-racks.

However, there are various problems in use of diethyltoluamide and therefore, the utilization thereof is limited to a defined range. A repellent is desired to have a vapour pressure of some degree so that the active ingredient may effectively vapourize, but if the vapourization is too extreme, the repellent effective time would be shortened. Under the circumstances, therefore, some particular treatment is required for vermin-repellent carpets and vermin-repellent furnitures which need the vermin-repellent effect for a long period of many years. The vapourization and reduction of the active ingredient is often influenced by the environmental light and temperature, and therefore the protection of the active ingredient is also required. Regarding vermin-repellents for application to human bodies, almost all of them are in the form of an aerosol type because the use is easy and the stability of the active ingredient and the preparation itself is good. However, such aerosol type vermin-repellents have defects that the active ingredient diffuses in air, and the active ingredient is absorbed into a body too rapidly through the skin so that the repellent effect could not last long on the skin. Moreover, a solvent such as an alcohol is added to the repellent preparation since diethyltoluamide is hardly soluble in water, and therefore, the preparation is stimulative to a wounded skin and it is flammable.

In order to overcome these defects of the diethyltoluamide-containing preparation, other means have been considered where diethyltoluamide is blended with an urethane resin or a cellulose derivative and coated on the wall of furnitures to form a hardened film thereon so as to prolong the effective life of diethyltoluamide coated, or a sweat-inhibiting substance is used together with diethyltoluamide for application to human bodies so as to reduce the endermic absorption of of diethyltoluamide and to prolong the effective life thereof coated on the skin. However, both of the said means were insufficient since the control of the vapourization speed of diethyltoluamide on the skin coated is difficult.

SUMMARY OF THE INVENTION

An object of the present invention is to provide slow-release vermin-repellent microcapsules filled with diethyltoluamide which may prevent the decrease of the pharmaceutical effect of diethyltoluamide under various circumstances and which may have a vermin-repellent effect against various insanitary vermin for a long period of time, diethyltoluamide of its original form being impossible to be effective for a long period of time.

Another object of the present invention is to provide slow-release vermin-repellent microcapsules filled with diethyltoluamide which have a microcapsule wall capable of freely adjusting the optimum vaporization speed in accordance with the insanitary vermin to be repelled by the microcapsule-containing preparation and the places to which the microcapsule-containing preparation is to be applied so that the vaporization of the diethyltoluamide as contained in the microcapsules is controlled to fall within the necessary lowermost range, whereby economical and effective utilization of the active ingredient diethyltoluamide may be attained.

Still another object of the present invention is to provide slow-release vermin-repellent microcapsules filled with diethyltoluamide which are solid granular or powdery preparations capable of being used for vermin-repellent application or treatment extremely easily as compared with diethyltoluamide of its original form, which is liquid. The microcapsules of the invention are stable in the form of a dispersion in water, but when used for vermin-repellent application or treatment, these could release the active ingredient diethyltoluamide through the walls of the microcapsules gradually and slowly because of the slow-releasability of the function of the microcapsules.

DETAILED DESCRIPTION OF THE INVENTION

The present inventors have paid an attention to the fact that diethyltoluamide of its original form is effective to be able to display its pharmaceutical effect for a period of only several hours and in addition, as the compound diethyltoluamide is liquid, the usable range thereof as an insecticide is limited although it has an effective insecticidal potency, and have researched in many ways. As a result, it has been found that above-mentioned objects of the present invention can be achieved by slow-release vermin-repellent microcapsules composed of a core substance and a wall film formed around the said core substance to envelop the same, in which the core substance is diethyltoluamide as represented by a structural formula:

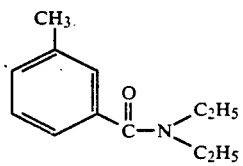

and the wall film has a function of slow-releasability.

In the microcapsules of the present invention, diethyltoluamide is microcapsulated with a wall film capable of freely controlling the vapourization speed of the core substance diethyltoluamide whereby diethyltoluamide is protected from the surrounding atmosphere so that the stability of the core substance diethyltoluamide may be improved. Further, the treatment with the microcapsules-containing preparation may be controlled to be the necessary lowermost limit. Accordingly, it is possible to prolong the effective vermin-repellent potency of the preparation for a long period of time even with a small amount of the active ingredient diethyltoluamide. Moreover, diethyltoluamide may be used in the form of solid grains. Accordingly, slow-release vermin-repellent microcapsules capable of being used for vermin-repellent processing or treatment with ease can be provided by the present invention.

As a method of microcapsulation of diethyltoluamide in which a core substance comprising diethyltoluamide only or a diethyltoluamide-containing mixture is encapsulated with a wall film which has a function of slow-releasability capable of controlling the vapourization speed of diethyltoluamide without lowering the pharmaceutical potency thereof, any known production technique can be employed. Examples of methods for preparing such microcapsules include an interfacial polymerization method, an in situ method, a coacervation method, a liquid-in-curing/coating method (an orifice method), a liquid-in-drying method and a spray/-graining method. In particular, the interfacial polymerization and the in situ method are especially advantageous as being able to effectively and economically prepare the intended diethyltoluamide microcapsules.

In accordance with the present invention, any and every substance which has a function of slow-releasability of diethyltoluamide can be used as the wall material for microcapsules. As an especially important point in selection of the wall material for microcapsules, materials which may control the degree of the slow-releasability of the core substance diethyltoluamide in a broad range without lowering the pharmaceutical potency of diethyltoluamide and also without lowering the strength of the microcapsules themselves because of the slow-releasability thereof are to be selected.

As materials which may satisfy the said object, high polymer materials formed from reactive materials such as monomers or low molecular prepolymers are especially preferred, and examples of such high polymer materials include polyamide resins, polyester resins, polyurea resins, polyurethane resins, urea resins, guanamine resins, melamine resins and complex materials thereof.

Some kinds of the above-mentioned high polymer materials could have a function of slow-releasability to the diethyltoluamide encapsulated as the core substance, by themselves, but some others of them could not have a function of sufficient slow-releasability when the core substance diethyltoluamide is encapsulated therewith by conventional microcapsulation techniques.

For instance, diethyltoluamide microcapsules with walls of a melamine resin, urea resin or polyamide resin could hardly have a sufficient slow-releasability for satisfactory vermin-repellent potency. In addition, even for wall materials having a function of slow-releasability to diethyltoluamide, the slow-releasability itself is required to be properly controlled. Under the circumstances, the present inventors have found that impartation and controlling of the slow-releasability of the wall materials may be attained by reducing the amount of the monomers and prepolymers to be used for the capsule wall materials.

As opposed to the fact that the reduction of the proportion of the wall material to the diethyltoluamide-containing core substance would result in the reduction of the retentive power and the protective power of the wall material for the liquid diethyltoluamide as encapsulated therewith, the present inventors have found that the reduction of the proportion of the wall material to the diethyltoluamide-containing core substance as limited only within a range capable of sufficiently maintaining the retentive power and the protective power of the wall material itself can create the possibility of impartation and adjustment of practical slow-releasability even in the wall materials which could not have a sufficient slow-releasability by conventional microcapsulation techniques. Specifically, a wall film made of a melamine resin material could not have a sufficient slow-releasability in microcapsules prepared by conventional methods so that this could not satisfy the object of the present invention. However, in accordance with the present invention, the amount of the monomers or prepolymers to be used for formation of the wall film is properly adjusted so that the resulting wall film formed may have a pertinent slow-releasability of a broad range without detracting from the strength of the wall film and the protective power thereof to protect the encapsulated core substance within a practical range. Accordingly, even when a melamine resin is used as the wall film material for encapsulation of the core substance diethyltoluamide, slow-release vermin-repellent microcapsules which may maintain the effect of repelling insanitary vermin for a long period of time can be obtained by the present invention.

As other methods for adjusting the slow-releasability of the diethyltoluamide-containing microcapsules of the present invention, there may be mentioned an encapsulation method where diethyltoluamide to be the core substance is blended with a high boiling point-solvent and the resulting blend is encapsulated, and a slow releasability-controlling method where a slow-release microcapsules-containing dispersion is dried by spray-drying to form a powder with adding a water-soluble high polymer or emulsion thereto so that the said material is coated on the surface of the capsule walls.

The preferred ratio of the diethyltoluamide-containing core substance to the wall material in the microcapsules of the present invention is not specifically limited, but in view of the economical aspect, the wall film material which does not have a direct vermin-repelling potency is better to be as small as possible. As mentioned above, however, since the microcapsule wall material of the present invention is required to sufficiently maintain the encapsulated liquid diethyltoluamide with simultaneously protecting the encapsulated substance, the lower limit of the amount of the wall film material to be used to the core substance would accordingly be limited. Under the circumstances, the preferred weight ratio of the core substance to the wall material is from 1/1 to 1/0.01, more preferably from 1/0.3 to 1/0.03. Accordingly, the variation of the amount of the monomers and prepolymers for the above-mentioned impartation or controlling of the slow-releasability in the wall film material is to be made within the said range.

When a melamine resin is used for formation of the wall film in the microcapsules of the present invention, the proportion of the melamine resin wall film to the core substance must necessarily be within the range of from 3 to 10% by weight, whereby diethyltoluamide-containing vermin-repellent microcapsules with sufficient slow-releasability can be obtained.

As the melamine resins to be used for formation of the wall film of the microcapsules of the present invention, any commercial prepolymers or any other melamine-formaldehyde prepolymers obtainable by heating melamine and formaline under an alkaline condition can be used. The molar ratio of melamine to formaldehyde is preferably within the range of from 1/1 to 1/4.

The grain size of the microcapsules of the present invention is preferably within the range of from 1 mm to $1\mu$, more preferably from $100\mu$ to $1\mu$, in view of the balance between the capsule strength and the degree of the slow-releasability.

In actual use of the diethyltoluamide-containing vermin-repellent slow-release microcapsules of the present invention, the microcapsules-containing dispersion may be coated, sprayed or penetrated into the places where insanitary vermin, such as cockroaches, acarids, fleas, lice, clothes moths or webbing clothes moths, museum beetles and ants, are required to be repelled out for a long period of time, in an amount of from 1 to 100 $g/m^2$, preferably from 3 to 70 $g/m^2$, as diethyltoluamide, or alternatively, the microcapsules are incorporated into a shaped tape or sheet and applied to the said places. Against biting vermin, such as mosquitos, gnats, flies, horseflies, rice-bran mosquitos, tsutsugamushi mites and acarids, the microcapsules of the present invention are used in the form of an aerosol, cream or lotion preparation containing from 0.5 to 40%, preferably from 2 to 30%, of diethyltoluamide, or alternatively, the microcapsules-containing dispersion may be used by itself.

Accordingly, the diethyltoluamide-containing vermin-repellent slow-release microcapsules-containing preparation of the present invention can be used widely and variously in the form of the microcapsules-containing dispersion by itself, or in the form of a microcapsules-containing powder, or even in other forms of powdery preparation, shaped preparation, ink preparation or coating preparation.

The following examples will serve to more fully illustrate the advantages of the present invention. Unless otherwise specifically indicated, the temperature as referred to herein is by °C. and the part and % as referred to herein are by weight.

EXAMPLE 1

31.6 parts of polymethylene polyphenylisocyanate (trade name MR-200; Nippon Polyurethane Co., Ltd.) were added to 135 parts of diethyltoluamide and dissolved, and the resulting solution was added to 300 parts of 2% polyvinyl alcohol (trade name PVA-217; Kuraray Co., Ltd.) solution and emulsified with Ultra-Homogenizer (manufactured by Nippon Seiki KK) to prepare an emulsion of grains having a grain size of $5\mu$. An aqueous solution obtained by previously dissolving 3 parts of diethylenetriamine in 40 parts of water was gradually added to the resulting emulsion with slowly stirring and then the whole was continuously stirred for about 20 hours at room temperature for sufficient reaction of the components to obtain a dispersion containing slow-release diethyltoluamide core/polyurea wall microcapsules.

EXAMPLE 2

31.6 parts of polymethylene polyphenylisocyanate (trade name MR-200; Nippon Polyurethane Co., Ltd.) were added to 135 parts of diethyltoluamide and dissolved, and the resulting solution was added to 300 parts of an aqueous 3% solution (pH 7.0) prepared by dissolving ethylene/maleic anhydride copolymer (trade name EMA-31; Monsanto Co., Ltd.) together with a small amount of sodium hydroxide and emulsified with Ultra-Homogener to obtain an emulsion of grains having a grain size of $4\mu$. The temperature of the thus obtained emulsion was elevated up to 65° C. and the emulsion was stirred for 2 hours to obtain a slow-release diethyltoluamide core/polyurethane wall microcapsules-containing dispersion.

EXAMPLE 3

10 parts of terephthalic acid chloride were added to 135 parts of diethyltoluamide and dissolved, and the resulting solution was added to 300 parts of 3% polyvinyl alcohol (trade name PVA-217; Kraray Co., Ltd.) solution and emulsified with Ultra-Homogenizer to obtain an emulsion of grains having a grian size of $5\mu$.

An aqueous solution obtained by previously dissolving 3.4 parts of ethylenediamine and 6 parts of soda ash in 70 parts of water was gradually added to the resulting emulsion with slowly stirring and then the whole was continuously stirred for about 20 hours at room temperature for sufficient reaction of the components to obtain a slow-release diethyltoluamide core/polyamide wall microcapsules-containing dispersion.

EXAMPLE 4

135 parts of diethyltoluamide were added to 200 parts of an aqueous 3% solution (pH 4.5) prepared by dissolving styrene-maleic anhydride resin (trade name Scripset 520; Monsanto Co., Ltd. together with a small amount of sodium hydroxide and then emulsified with Ultra-Homogenizer to obtain an emulsion of grains having a grain size of $10\mu$.

14.8 parts of benzoguanamine and 16.7 parts of an aqueous 37% formaldehyde solution were added to 65 parts of water and an aqueous 20% sodium hydroxide solution was added thereto to make pH of being 9.5. The whole was heated at 80° C. for 15 minutes to prepare benzoguanamine/formaldehyde prepolymer. This was added to the above-mentioned emulsion and stirred for 2 hours at a liquid temperature of 75° C. to obtain a slow-release diethyltoluamide core/benzoguanamine resin wall microcapsules-containing dispersion.

EXAMPLE 5

The slow-release diethyltoluamide core/benzoguanamine resin wall microcapsules-containing dispersion obtained in Example 4 was diluted to 20% concentration and then spray-dried with a spray drier (trade name DL-41 Type; Yamato Chemical Co., Ltd.) under the condition of the inlet temperature of 250° C., the nozzle pressure of 1.5 kg/m² and the sample-feeding rate of 20 g/min, to obtain a slow-release diethyltoluamide microcapsule powder.

EXAMPLE 6

8.1 parts of melamine and 6.8 parts of an aqueous 37% formaldehyde solution were used in place of 14.8 parts of benzoguanamine and 16.7 parts of aqueous 37% formaldehyde solution in Example 1, and a slow-release diethyltoluamide core/melamine resin wall microcapsules-containing dispersion was thereby obtained.

COMPARATIVE EXAMPLE 1

135 parts of diethyltoluamide were added into 300 parts of the solution of 3% polyvinyl alcohol(trade name PVA-217; Kraray Co., Ltd.) and emulsified with Ultra-Homogenizer to obtain an emulsion of grains having a grain size of 5 and thus an emulsion of diethyltoluamide was obtained.

The results of time-dependent stability test of diethyltoluamide microcapsules-containing dispersions obtained in Examples 1 to 6 and diethyltoluamide-emulsified dispersions obtained in Comparative Example 1 are shown in Table 1, the results of slow-releasability test of these dispersions are in Table 2, and the results of insanitary vermin-repellent test are in Tables 3, 4 and 5.

TABLE 1

Residual Percentage of Diethyltoluamide in Microcapsules in Water Dispersion Six Months After Encapsulation

| | Wall Material | Residual Percentage (%)(*) of Diethyltoluamide 6 months after Encapsulation |
|---|---|---|
| Example 1 | Polyurea Resin | 98 |
| Example 2 | Polyurethane Resin | 98 |
| Example 3 | Polyamide Resin | 99 |
| Example 4 | Benzoguanamine Resin | 100 |
| Example 5 | Melamine Resin | 100 |
| Comparative Example 1 | Emulsion | 100 |

(*) Percentage (%) to the amount of diethyltoluamide one day after encapsulation.

Method of measuring the amount of diethyltoluamide in microcapsules 3 ml of each of the diethyltoluamide microcapsules-containing dispersions prepared in Examples 1 to 6 was taken out and filtered. 9 ml of acetone was added to the thus isolated microcapsules and the diethyltoluamide was extracted out therefrom by ultrasonic treatment. Then the amount of the thus extracted diethyltoluamide was measured in accordance with DEET purity test method as a standard method for insecticides.

TABLE 2

Slow-Releasability of Diethyltoluamide Core Microcapsules

| | % (after 1 month) | % (after 3 months) |
|---|---|---|
| Example 1 | 70.1 | 45.0 |
| Example 2 | 58.1 | 30.2 |
| Example 3 | 53.8 | 27.0 |
| Example 4 | 48.2 | 16.6 |
| Example 5 | 70.3 | 52.6 |
| Example 6 | 42.2 | 13.0 |
| Comparative Example 1 | 0 | 0 |

Method of Evaluation of Slow-Releasability

Each of the diethyltoluamide microcapsules-containing dispersions and diethyltoluamide-emulsified dispersions prepared in Examples 1 to 6 and Comparative Example 1 were coated on a synthetic paper (trade name Yupo #130; Ohji Yuka Synthetic Paper Co. Ltd.) size 10×10 cm) in an amount of about 5 g/m² as diethyltoluamide and dried. On the other hand, each of the diethyltoluamide microcapsules-containing powder samples was uniformly spread on a watch glass in an amount of about 1 g. Each sample was put in an atmosphere of 23° C. and the residual percentage of diethyltoluamide was measured after a certain period of time.

TABLE 3

| Cockroach (Blattella) Repellent Test | | |
|---|---|---|
| | Effective Repellent Life (days) | |
| Amount of Diethyltoluamide | 5 g/m² | 10 g/m² |
| Diethyltoluamide of Original Form | 7 | 14 |
| Example 1 | 16 | 86 |
| Example 2 | 21 | 88 |
| Example 3 | 35 | 90 |
| Example 4 | 34 | 90 |
| Example 6 | 38 | 95 |

Method of Testing the Effect of Cockroach (Blattella) Repellent

Cockroaches (Blattella) were kept on plywoods (10×10 cm) for one month. Diethyltoluamide of its original form or each of the diethyltoluamide microcapsules-containing dispersions prepared in Examples 1 to 4 and 6 was coated on both surfaces of the plywoods each in an amount of 5 g/m² or 10 g/m² as diethyltoluamide. The thus coated plywoods were dried for one full day. Then the plywoods were layered together with plywoods not coated with the chemical agent as put between the coated plywoods with an interval of 1.5 cm. The thus layered plywood construction was put in a plastic container and 100 cockroaches (Blattella) (male imagos/female imagos/larvae=1/1/1) were put in the container. These cockroaches were observed, and the first day when some cockroaches approached the plywood construction was checked. The time from the day when the chemical agent had been coated on the plywood to the day when some cockroaches had first approached the plywood in the plastic container was counted, which is the effective repellent life (days) shown in Table 3 above.

TABLE 4

| Mosquito (Culex) Repellent Test | |
|---|---|
| Diethyltoluamide of Original Form | Effective Repellent Life 5.75 hr |
| Example 1 | >24 hr |
| Example 3 | >24 hr |
| Example 4 | >24 hr |
| Example 6 | >24 hr |

Method of Testing the Effect of Mosquito (Culex) Repellent:

Diethyltoluamide of its original form or each of the diethyltoluamide microcapsules-containing dispersions prepared in Examples 1, 3, 4 and 6 was uniformly applied to test persons each on its one forearm in an amount of 1 g as diethyltoluamide. The forearm was inserted into a cage containing mosquitos (Culex) for 3 minutes with an interval of about 30 minutes, and the time when the forearm was first bitten by mosquitos was checked. The period from the time when the chemical agent had been applied to the forearm to the time when the forearm had first been bitten by mosquitos was measured, which is the effective repellent life (hours) shown in Table 4 above. The repellent test was carried out for 24 hours, and when the forearm was not bitten even after the lapse of 24 hours, the effective repellent life was shown to be "more than 24 hours (>24 hr)" in Table 4.

TABLE 5

| Acarid (Tyroglyphus) Repellent Test | | | | | |
|---|---|---|---|---|---|
| | Number of Living Acarids on Black Paper | | | | |
| Diethyltoluamide of Original Form | After 1 day 32 | 14 days 196 | 1 month 494 | 2 months 875 | 3 months 1732 |
| Example 1 | 0 | 0 | 0 | 0 | 0 |
| Example 3 | 0 | 0 | 0 | 0 | 0 |
| Example 6 | 0 | 0 | 0 | 0 | 0 |

Method of Testing the Effect of Acarid (Tyroglyphus Repellent

A carpet which had been treated with no vermin-repellent was cut into 7×7 cm pieces, and diethyltoluamide of its original form or each of the diethyltoluamide microcapsules-containing dispersions prepared in Examples 1, 3 and 6 was uniformly coated on the surface of each carpet piece in an amount of 5 g/m² as diethyltoluamide and then dried for one full day. Then the chemical-treated carpet piece and a non-treated carpet piece were put in parallel on an enamelled vat as set in a chamber under the condition of 25 ° C. and 90%(RH) or more. 2.0 g of a powdery feed (water content: 15%) was uniformly put on the surface of each carpet piece. A small amount of a medium where acarids (Tyroglyphus) had greatly propagated was put between the carpet pieces.

For observation of the acarid-repelling effect of the chemical agents tested, a 5×5 cm black flockpaper was put over each carpet piece one day, 14 days, one month, two months and 3 months after inoculation of acarids (Tyroglyphus), and the number of the living acarids on both surfaces of the black paper was counted.

EXAMPLE 7

135 parts of diethyltoluamide were added to 200 parts of an aqueous 3% solution (pH 4.5) prepared by dissolving styrene-maleic anhydride resin (trade name Scripset 520; Monsanto Co., Ltd.) together with a small amount of sodium hydroxide and then emulsified with Ultra-Homogenizer to obtain an emulsion of grains having a grain size of 10μ.

6.0 parts of melamine and 15.0 parts of an aqueous 37% formaldehyde solution were added to 65 parts of water and an aqueous 20% sodium hydroxide solution was added thereto.

COMPARATIVE EXAMPLE 2

Fifteen parts of terephthalic acid chloride was added to and dissolved in 135 parts of diethyltoluamide, and the mixture was then added to 300 parts of a 3% polyvinyl alcohol (trade name PVA-216; made by Kuraray Co., Ltd.) solution. Afterward, emulsification was carried out by means of an ultrahomogenizer so that the particle diameter of the resulting emulsion might be 5 μm.

To the thus obtained emulsion, with slow stirring, was gradually added an aqueous solution previously prepared by dissolving 8.8 parts of diethylenetriamine and 9 parts of soda ash in 70 parts of water, and stirring was continued at room temperature for about 20 hours in order to sufficiently perform a reaction, thereby obtaining a dispersion of polyamide wall microcapsules having slow-release potentiality and embracing diethyltoluamide.

COMPARATIVE EXAMPLE 3

First, 31.6 parts of polymethylene polyphenylisocyanate (trade name MR-200; made by Nippon Polyurethane Industry Co., Ltd.) was added to and dissolved in 135 parts of diethyltoluamide, and the mixture was then added to 300 parts of a 3% aqueous solution having a pH=7 previously prepared by dissolving an ethylene-maleic anhydride copolymer (trade name EMA-31; made by Monsanto Chemical Co.) in a small amount of sodium hydroxide. Afterward, emulsification was carried out by means of an ultrahomogenizer so that the particle diameter of the resulting emulsion might be 4 μm. The temperature of the thus obtained emulsion was raised up to 65° C. and stirring was carried out for 2 hours, thereby obtaining a dispersion of polyurethane wall microcapsules having slow-release potentiality and embracing diethyltoluamide.

COMPARATIVE EXAMPLE 4

Twenty parts of urea and 2 parts of resorcin were dissolved in a 10% aqueous solution of an ethylene-maleic anhydride copolymer (trade name EMA-31; made by Monsanto Chemical Co.), and 200 parts of water was added thereto. By the use of a 20% aqueous sodium hydroxide solution, the pH of the mixture was adjusted to 3.5, and 135 parts of diethyltoluamide was then added thereto. Afterward, emulsification was carried out by means of an ultrahomogenizer so that the particle diameter of the resulting emulsion might be 5 μm. A 37% aqueous formaldehyde solution was then added to the thus obtained emulsion, and the temperature of the solution was raised up to 55° C. and was then stirred for 2 hours, thereby obtaining a dispersion of microcapsules having urea resin wall films and embracing diethyltoluamide.

EXAMPLE 12

The slow-release diethyltoluamide core/melamine resin wall microcapsules-containing dispersion obtained in Example 9 was diluted to 20% concentration and then spray-dried with a spray drier (trade name DL-41 Type; Yamato Chemical Co., Ltd.) under the condition of the inlet temperature of 250° C., the nozzle pressure of 1.5 kg/m2 and the sample-feeding rate of 20 g/min, to obtain a slow-release diethyltoluamide microcapsule powder.

Results of Evaluation of Samples

The samples prepared above were tested and the results obtained were shown in Tables 7 to 11 below.

TABLE 7

Residual Percentage (%) of Diethyltoluamide (DETAM) in Microcapsules in Water Dispersion Immediately after Encapsulation and Six Months after Encapsulation

|  | Wall Material | Wall (%) | Residual DETAM (%) () Immediately after Encapsulation | Residual DETAM (%) (*) Six Months after Encapsulation |
|---|---|---|---|---|
| Example 7 | Melamine Resin | 8.6 | 99 | 99 |
| Example 8 | Melamine Resin | 5.7 | 99 | 99 |
| Example 9 | Melamine Resin | 3.5 | 99 | 99 |
| Example 10 | Melamine Resin | 19.3 | 100 | 100 |
| Example 11 | Melamine Resin | 12.0 | 99 | 99 |
| Comparative Example 2 | Polyamide Resin | 17.6 | 65 | 64 |
| Comparative Example 3 | Polyurethane Resin | 23.4 | 80 | 78 |
| Comparative Example 4 | Ureaformaldehyde Resin | — | 90 | 90 |

Wall (%) = Proportion (wt. %) of wall to core substance
(**) Proportion (%) of residual diethyltoluamide core to diethyltoluamide as originally incorporated, immediately after encapsulation.
(***) Proportion (%) of residual diethyltoluamide core to diethyltoluamide as originally incorporated, 6 months after encapsulation.

Method of measuring the amount of diethyltoluamide in microcapsules 3 ml of each of the diethyltoluamide microcapsules-containing dispersions prepared in Examples 7 to 11 and Comparative Examples 2 to 4 was taken out and filtered. 9 ml of acetone was added ot the thus isolated microcapsules and the diethyltoluamide was extracted out therefrom by ultrasonic treatment. Then the amount of the thus extracted diethyltoluamide was measured in accordance with DEET purity test method as a standard method for insecticides.

TABLE 8

Slow-Releasability of Diethyltoluamide Core Microcapsules

|  | % (after 1 month) | % (after 3 months) |
|---|---|---|
| Example 7 | 82.9 | 55.8 |
| Example 8 | 61.3 | 32.4 |
| Example 9 | 40.5 | 11.7 |
| Comparative Example 3 | 99.6 | 99.4 |
| Comparative Example 4 | 97.0 | 91.3 |

Method of Evaluation of Slow-Releasability

Each of the diethyltoluamide microcapsules-containing dispersions prepared in Examples 7 to 9 and Comparative Examples 3 and 4 was coated on a synthetic paper (trade name Yupo #130; Ohji Yuka Synthetic Paper Co., Ltd.) (size 10×10 cm) in an amount of about 5 g/m² as diethyltoluamide and dried. On the other hand, each of the diethyltoluamide microcapsules-containing powder samples was uniformly spread on a watch glass in an amount of about 1 g. Each sample was put in an atmosphere of 23° C. and the residual percentage of diethyltoluamide was measured after a certain period of time.

TABLE 9

Cockroach (Blattella) Repellent Test

| Amount of Diethyltoluamide | Effective Repellent Life (days) | |
|---|---|---|
| | 5 g/m² | 10 g/m² |
| Diethyltoluamide of Original Form | 7 | 14 |
| Example 7 | 30 | 143 |
| Example 8 | 40 | 102 |
| Example 9 | 35 | 90 |
| Comparative Example 3 | 0 | 0 |
| Comparative Example 4 | 0 | 0 |

Method of Testing the Effect of Cockroach (Blattella) Repellent

Cockroaches (Blattella) were kept on plywoods (10×10 cm) for one month. Diethyltoluamide of its original form or each of the diethyltoluamide microcapsules-containing dispersions prepared in Examples 7 to 9 and Comparative Examples 3 and 4 was coated on both surfaces of the plywoods each in an amount of 5 g/m² or 10 g/m² as diethyltoluamide. The thus coated plywoods were dried for one full day. Then the plywoods were layered together with plywoods not coated with the chemical agent as put between the coated plywoods with an interval of 1.5 cm. The thus layered plywood construction was put in a plastic container and cockroached (Blattella) (male imagos/female imagos/larvae=1/1/1) were put in the container. These cockroaches were observed, and the first day when some cockroaches approached the plywood construction was checked. The time from the day when the chemical agent had been coated on the plywood to the day when some cockroaches had first approached the plywood in the plastic container was counted, which is the effective repellent life (days) shown in Table 9 above.

TABLE 10

Mosquito (Culex) Repellent Test

| Diethyltoluamide of Original Form | Effective Repellent Life 5.75 hr |
|---|---|
| Example 7 | >24 hr |
| Example 8 | >24 hr |
| Example 9 | >24 hr |
| Comparative Example 3 | 0 hr |
| Comparative Example 4 | 0 hr |

Method of Testing the Effect of Mosquito (Culex) Repellent

Diethyltoluamide of its original form or each of the diethyltoluamide microcapsules-containing dispersions prepared in Examples 7 to 9 and Comparative Examples 3 and 4 was uniformly applied to test persons each on its one forearm in an amount of 1 g as diethyltoluamide. The forearm was inserted into a cage containing mosquitos (Culex) for 3 minutes with an interval of about 30 minutes, and the time when the forearm was first bitten by mosquitos was checked. The period from the time when the chemical agent had been applied to the forearm to the time when the forearm had first been bitten by mosquitos was measured, which is the effective repellent life (hours) shown in Table 10 above. The repellent test was carried out for 24 hours, and when the forearm was not bitten even after the lapse of 24 hours, the effective repellent life was shown to be "more than 24 hours (>24 hours)" in Table 10.

TABLE 11

Acarid (Tyroglyphus) Repellent Test

| | Number of Living Acarids on Black Paper | | | | |
|---|---|---|---|---|---|
| | After 1 day | 14 days | 1 month | 2 months | 3 months |
| Diethyltoluamide of Original Form | 32 | 196 | 494 | 875 | 1732 |
| Example 7 | 0 | 0 | 0 | 0 | 0 |
| Example 8 | 0 | 0 | 0 | 0 | 0 |
| Example 9 | 0 | 0 | 0 | 0 | 0 |
| Comparative Example 3 | 27 | 189 | 498 | 890 | 1692 |
| Comparative Example 4 | 34 | 190 | 512 | 860 | 1810 |

Method of Testing the Effect of Acarid (Tyroglyphus) Repellent

A carpet which had been treated with no vermin-repellent was cut into 7×7 cm pieces, and diethyltoluamide of its original form or each of the diethyltoluamide microcapsules-containing dispersions prepared in Examples 7 to 9 and Comparative Examples 3 and 4 was uniformly coated on the surface of each carpet piece in an amount of 5 g/m² as diethyltoluamide adn then dried for one full day. Then the chemical-treated carpet piece and a non-treated carpet piece were put in parallel on an enamelled vat as set in a chamber under the condition of 25° C. and 90%(RH) or more. 2.0 g of a powdery feed (water content: 15%) was uniformly put on the surface of each carpet piece. A small amount of a medium where acarids (Tyroglyphus) had greatly propagated was put between the carpet pieces.

For observation of the acarid-repelling effect of the chemical agents tested, a 5×5 cm black flockpaper was put over each carpet piece one day, 14 days, one month, two months and 3 months after inoculation of acarids (Tyroglyphus), and the number of the living acarids on both surfaces of the black paper was counted.

As is obvious from the results in Table 1, the slow-release diethyltoluamide-containing microcapsules of the present invention are possible to maintain the core substance diethyltoluamide extremely stably in an aqueous dispersion, although these are slow-releasable microcapsules. Accordingly, the slow-releasing function of the microcapsules can be attained only when the water component has been removed out after the microcapsules-containing dispersion was applied to the places where insanitary vermin are required to be repelled. Therefore, the stability of the core substance diethyltoluamide in the microcapsules may be kept for a very long period of time and the slow-releasing function of the microcapsules can be attained at any necessary time.

Tables 2 to 5 and 8 to 11 demonstrate that the vapourization of the active ingredient diethyltoluamide may freely be controlled, especially to the necessary lowermost limit, if desired. Accordingly, as compared with diethyltoluamide of its original form, the diethyltoluamide-containing microcapsules of the present invention may keep the insanitary vermin-repelling potency for an extremely long period of time because of the advantageous slow-releasability. Therefore, the microcapsules of the present invention can be applied to various fields of a broad range where the vermin-repelling effect is required to last for a long period of time or where the conventional vermin-repellents could not be applied because of the short repellent life, for example, vermin-repellent carpets, vermin-repellent tatamis (Japanese carpets), vermin-repellent furnitures or vermin-repellent plate-racks.

In accordance with the present invention, the vapourizing rate of the active substance diethyltoluamide may freely and easily be controlled in accordance with the situation for application of vermin-repellent, the objective vermin to be repelled, the space for application of vermin-repellent, the potency of vermin-repellent to be used and the environment for application of vermin-repellent, without any complicated operation or treatment as required in use of conventional vermin-repellents. Accordingly, even an extremely small amount of the vermin-repellent microcapsules of the present invention suffices for repelling of various insanitary vermin, and the microcapsules of the invention can be used extremely economically with ease.

In accordance with the present invention, since a liquid diethyltoluamide may be formed into solid grains or powder which may be handled with ease, and the processability of diethyltoluamide is extremely improved. The diethyltoluamide of a solid form may therefore be processed into a coating composition with ease or may be applied to an adhesive tape or the like base body also with ease.

In addition, the low toxicity of diethyltoluamide may be reduced more because of encapsulation thereof, and accordingly, the present invention can provide diethyltoluamide microcapsules with high safety.

In particular, as is obvious from the results in Table 7, the slow release diethyltoluamide core/melamine resin wall microcapsule vermin repellents of the present invention are extremely excellent in the diethyltoluamide-retentiveness, and these are possible to maintain the core substance diethyltoluamide extremely stably in an aqueous dispersion, although these are slow-releasable microcapsules. Accordingly, the slow-releasing function of the microcapsules can be attained only when the water component has been removed out after the microcapsules-containing dispersion was applied to the places where insanitary vermin are required to be repelled. Therefore, the stability of the core substance diethyltoluamide in the microcapsules may be kept for a very long period of time and the slow-releasing function of the microcapsules can be attained at any necessary time.

What is claimed is:

1. A process for producing slow-release vermin-repellent microcapsules having an increased repellent lifetime comprising the steps of:
providing a core substance wherein said core substance is N,N-diethyl-m-toluamide as represented by a structural formula:

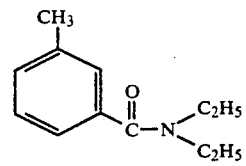

encapsulating said core substance in a wall film being formed of a melamine resin which slowly releases said core substance such that about 11.7%–about 55.8% of said core substance remains microencapsulated after a time period of at least three months; and wherein the proportion of said melamine resin to said core substance range from about 3% to 10% by weight.

2. Slow release vermin-repellent microcapsules having an increase repellent lifetime composed of a core substance and a wall film formed around said core substance to encapsulate the same, in which the core substance is N,N-diethyl-nm-toluamide as represented by a structural formula:

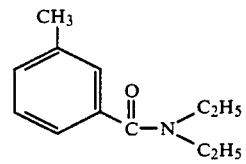

the wall film being formed of a melamine resin which slowly releases said core substance such that about 11.7%–about 55.8% of said core substance remains microencapsulated after a time period of at least three months; the proportion of said melamine resin to said core substance being in the range of about 3% to 10% by weight.

3. A method of applying slow-release vermin repellent microcapsules to areas from which vermin are to be repelled comprising the step of
contacting a chemically effective amount of said vermin repellent microcapsules of claim 2 to areas from which vermin are to be repelled.

* * * * *

UNITED STATES PATENT AND TRADEMARK OFFICE
CERTIFICATE OF CORRECTION

PATENT NO. : 5,039,524

DATED : August 13, 1991

INVENTOR(S) : Ryuichi Oishi, Keiichi Utaka, Kumiko Ono, Michihiro Ohki and Toshirou Yasue It is certified that error appears in the above-identified patent and that said Letters Patent is hereby corrected as shown below:

Column 1, line 8, "with N,N-diethyl m-toluamide" should read --with N,N-diethyl-m-toluamide--.

Column 1, line 22, "gnats, lies, horseflies" should read --gnats, flies, horseflies-.

Column 7, line 38, "Scripset 520; Monsanto Co., Ltd." should read --Scripset 520; Monsanto Co., Ltd.)--.

Column 8, line 32, "diethytoluamide" should read --diethyltoluamide--.

Column 8, line 35-36, "Method of measuring the amount of diethyltoluamide in microcapsules" should read --<u>Method of measuring the amount of diethyltoluamide in microcapsules:</u>--.

Column 8, line 59, "Method of Evaluation of Slow-Releasability" should read --<u>Method of Evaluation of Slow-Releasability:</u>--.

Column 8, line 66, "size 10X10 cm)" should read --(size 10 x 10 cm)--.

Column 9, lines 18-19, "Method of Testing the Effect of Cockroach (Blattella) Repellent" should read --<u>Method of Testing the Effect of Cockroach (Blattella) Repellent:</u>--.

Column 9, lines 51-52, "Method of Testing the Effect of Mosquito (Culex) Repellent:" should read --<u>Method of Testing the Effect of Mosquito (Culex) Repellent:</u>--.

UNITED STATES PATENT AND TRADEMARK OFFICE
CERTIFICATE OF CORRECTION

PATENT NO. : 5,039,524
DATED : August 13, 1991
INVENTOR(S) : Ryuichi Oishi, Keiichi Utaka, Kumiko Ono, Michihiro Ohki and Toshirou Yasue It is certified that error appears in the above-identified patent and that said Letters Patent is hereby corrected as shown below:

Column 10, lines 14-15, "Method of Testing the Effect of Acarid (Tyroglypus Repellent" should read --Method of Testing the Effect of Acarid (Tyroglypus) Repellent:--.

Column 10, line 57, "trade name PVA-216;" should read --trade name PVA-217--.

Column 12, line 1, "Results of Evaluation of Samples" should read --Results of Evaluation of Samples:--.

Column 12, line 31, "Method of measuring The amount of diethyltoluomide in microcapsules" should read --Method of measuring The amount of diethyltoluomide in microcapsules:--.

Column 12, line 56, "Method of Evaluation of Slow-Releasability" should read --Method of Evaluation of Slow-Releasability:--.

Column 13, line 15, "Method of Testing the Effect of Cockroach (Blattela) Repellent" should read --Method of Testing the Effect of Cockroach (Blattella) Repellent:--.

Column 13, line 51-52, "Method of Testing the Effect of Mosquito (Culex) Repellent" should read --Method of Testing the Effect of Mosquito (Culex) Repellent:--.

UNITED STATES PATENT AND TRADEMARK OFFICE
CERTIFICATE OF CORRECTION

PATENT NO. : 5,039,524

DATED : August 13, 1991

INVENTOR(S) : Ryuichi Oishi, Keiichi Utaka, Kumiko Ono, Michihiro Ohki and Toshirou Yasue It is certified that error appears in the above-identified patent and that said Letters Patent is hereby corrected as shown below:

Column 14, line 17-18, "Method of Testing the Effect of Acarid (Tyroglyphus) Repellent" should read --Method of Testing the Effect of Acarid (Tyroglyphus) Repellent:--.

Column 16, line 24, "having an increase repellent" should read --having an increased repellent--.

Column 16, line 27, "substance is N,N-diethyl-nm-" should read --substance is N,N-diethyl-m- --.

Column 16, line 21, "core substance range from" should read --core substance ranges from --.

Column 16, line 47, "the step of" should read --the step of:--.

Signed and Sealed this

Thirteenth Day of April, 1993

Attest:

STEPHEN G. KUNIN

*Attesting Officer*     *Acting Commissioner of Patents and Trademarks*